US00PP25017P2

(12) United States Plant Patent
Heims

(10) Patent No.: US PP25,017 P2
(45) Date of Patent: Oct. 28, 2014

(54) ***BEGONIA* PLANT NAMED 'PAINTER'S PALETTE'**

(50) Latin Name: *Begonia rex-cultorum*
Varietal Denomination: Painter's Palette

(71) Applicant: Terra Nova Nurseries, Inc., Canby, OR (US)

(72) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 32 days.

(21) Appl. No.: 13/986,387

(22) Filed: Apr. 26, 2013

(51) Int. Cl.
*A01H 5/00* (2006.01)

(52) U.S. Cl.
USPC ..... Plt./343

(58) Field of Classification Search
CPC ..... A01H 5/0238
USPC ..... Plt./343
See application file for complete search history.

*Primary Examiner* — June Hwu
*Assistant Examiner* — Keith Robinson
(74) *Attorney, Agent, or Firm* — Klarquist Sparkman, LLP

(57) ABSTRACT

A new and distinct form of *Begonia* plant characterized by multicolored broad leaves that are olive green with silver interveinal white blotches and a dark pink center overlay that covers the whole leaf in the cool season to the center ⅔ in the warm season, maroon leaf backs, a bushy habit, light pink flowers in winter to early spring, tolerant of cool temperatures to 33° F., and excellent vigor.

1 Drawing Sheet

Botanical denomination: *Begonia rex-cultorum.*
Variety designation: 'Painter's Palette'.

BACKGROUND

The present invention relates to a new and distinct cultivar of *Begonia*, of the family Begoniaceae, and given the cultivar name, 'Painter's Palette'. The new cultivar originated from a cross between unknown *Begonia rex-cultorum* parents. This selection is uniquely characterized by:

1. multicolored broad leaves
2. leaves olive green with silver interveinal white blotches and a dark pink center overlay that covers the whole leaf in the cool season to the center ⅔ in the warm season,
3. maroon leaf backs,
4. a bushy habit,
5. light pink flowers in winter to early spring,
6. tolerant of cool temperatures to 33° F., and
7. excellent vigor.

Compared to *Begonia* 'Salsa', U.S. Plant Pat. No. 22,339, the new cultivar has leaves that are much larger, with similar coloring to *Begonia* 'Salsa' in the warm season.

The new variety has been reproduced only by asexual propagation (leaf cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers and leaf of *Begonia* 'Painter's Palette'.

FIG. 2 shows a 1-and-a-half year old plant in a growing in a one gallon container in August in Canby. Oreg.

DETAILED PLANT DESCRIPTION

The following is a detailed description of the new *Begonia* cultivar based on observations of one year-old specimens grown in one gallon containers in a cool greenhouse in early February in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5$^{th}$ edition, 2007.

Plant:
- *Type*.—Herbaceous rhizomatous perennial.
- *Form*.—Clumping, caulescent.
- *Cold hardiness*.—USDA Zone 10a.
- *Size*.—Grows to 36 cm tall and 41 cm wide.
- *Vigor*.—Excellent.
- *Roots and rooting*.—Roots appear on leaf cuttings in 2 weeks; fine, fibrous, and white in color.

Stem:
- *Type*.—Upright, congested.
- *Size*.—Grows to 12 cm long and 20 mm wide.
- *Lateral branches*.—None.
- *Internodes*.—From 7 mm to 1 cm long.
- *Surface*.—Pubescent.
- *Color*.—Brown 200A.

Leaf:
- *Type*.—Simple.
- *Arrangement*.—Alternate, congested.
- *Number*.—About 100.
- *Shape*.—Broadly ovate, oblique.
- *Margins*.—Coarsely serrate.
- *Apex*.—Acuminate.
- *Base*.—Oblique.

*Venation*.—Palmate, Brown 200A on topside, bottom side Red Purple 59A.

*Blade size*.—Grows to 13 cm wide and 19.5 cm long.

*Surface texture*.—Pubescent on top and bottom.

*Leaf strength*.—Excellent, tough, somewhat brittle.

*Stipules*.—Deciduous, ovate-lanceolate, 20 mm long and 8 mm wide, apex acuminate and cuspidate, base clasping, entire, back side pubescent, inside glabrous, both sides Red Purple 60A.

*Petiole description*.—Grows to 21 cm long and 7 mm wide, succulent, pubescent, Greyed Purple 187A.

*Leaf color*.—Top side Black 202A along veins lightening to Green N137A on outside ⅓, spots of silver Black 202D between the veins, the center ⅔ of the leaf has a surface color of Red Purple 61A, Black 202A leaf margins; bottom side Purple 59A.

Inflorescence:

*Type*.—Axillary, bisexual, cymose.

*Number of flowers per cyme*.—Usually 6.

*Peduncle description*.—Grows 16 cm long and 4 mm wide, glabrous, fleshy, of good strength, Greyed Purple 184A; with 2 opposite, dehiscent petiolate leaf-bracts below each cyme, which grow to 4 mm wide and 9 mm long, margins entire, tip apiculate, back side pubescent, inside glabrous, both sides Greyed Red 181D.

*Pedicel description*.—Grow to 20 mm long, 1.5 mm wide, fleshy, of good strength, pubescent, Purple 75C on staminate flowers, Greyed Orange 177B on pistillate flowers.

*Bloom period*.—Early winter in Canby, Oreg.

Flower bud:

*Size*.—Staminate flowers 15 mm long and 11 mm wide prior to opening; pistillate flowers are 11 mm deep and 9 mm wide prior to opening.

*Shape*.—Teardrop.

*Surface texture*.—Pubescent.

*Color*.—Red Purple 62D overall and 62A on top center on tepal area, Greyed Orange 174A on ovary.

Flower:

*Type*.—Monoecious, bilaterally symmetrical.

*Pistillate flower*.—Grows to 20 mm deep and 39 mm wide overall; 5 fleshy tepals, grow to 16 mm long and 16 mm wide, broadly ovate, tip and base obtuse, margins entire, glabrous on both sides, outer tepals Red Purple 75B on inside and 62B outside, inner tepals Red Purple 62D on both sides except up the middle on back side where 63B; pistil 1, 13 mm long, ovary to 22 mm wide and 7 mm deep, three winged, two equal and one longer, Greyed Red 182A, style 2 branched, 2 mm long and Greyed Red 182C, stigma 3 branched and twisted, stigma 4 mm deep and 9 mm wide overall, Greyed Yellow 160A.

*Staminate flower*.—7 mm deep and 25 mm wide, 4 tepals, 2 larger outer tepals 14 mm long and 12 mm wide, cupped, broadly elliptical, margin entire, glabrous on both sides, tip obtuse, base truncate, Purple 75B inside and 75D outside; inner tepals grow to 12 mm long and 9 mm wide, oblong, entire, tip obtuse, base attenuate, both sides Red Purple 69D; stamen many in a globular head 4 mm in diameter, filament less than 1 mm long, anthers 1 mm long and Red Purple 65D, anthers and pollen Yellow 11C.

*Fragrance*.—None.

*Lastingness*.—A cyme blooms for about 4 weeks on the plant, flowers are self-cleaning.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

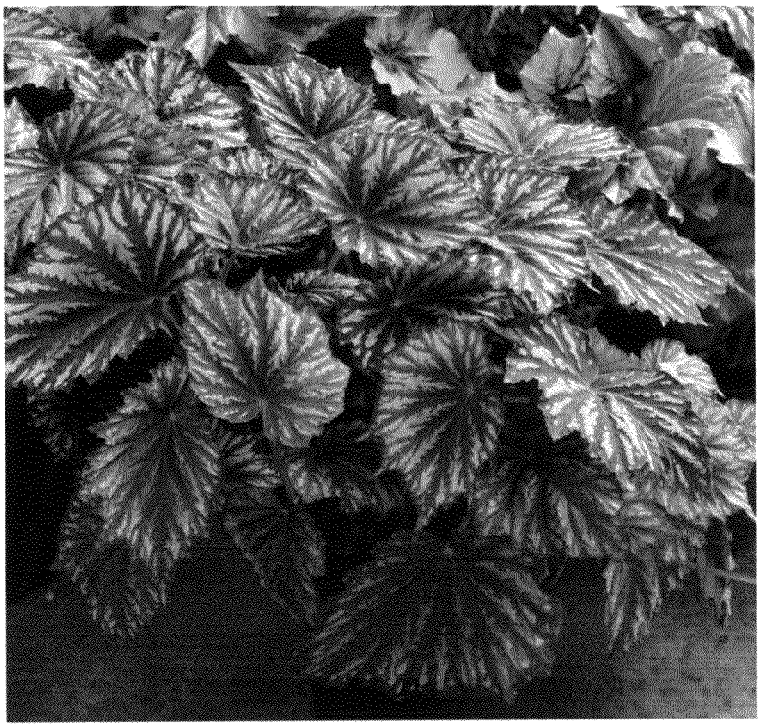

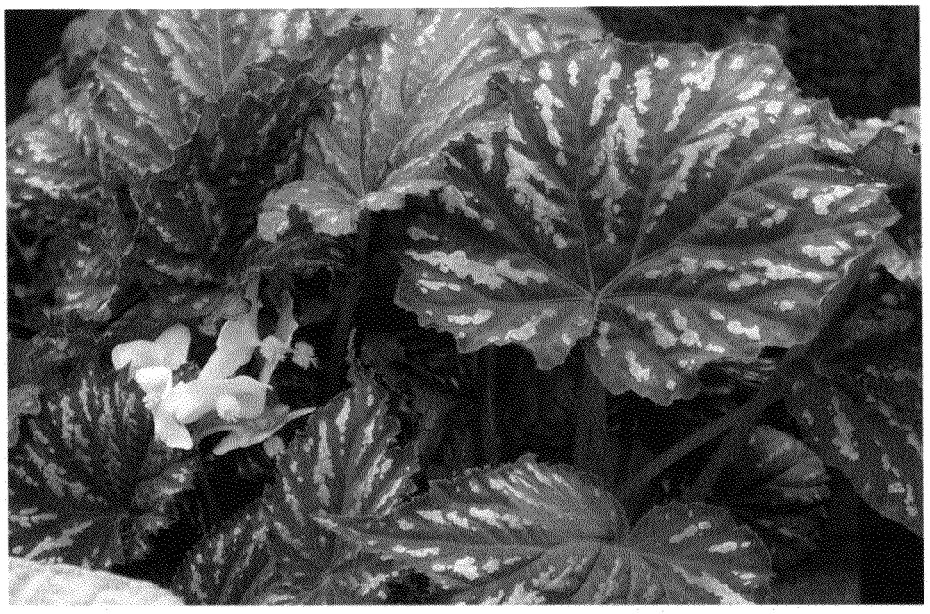
FIG. 1 above, FIG. 2 below